United States Patent [19]
Olson

[11] Patent Number: 4,601,715
[45] Date of Patent: Jul. 22, 1986

[54] CHEST DRAINAGE DEVICE WITH SOUND MUFFLING TUBE

[75] Inventor: Daniel H. Olson, Louisville, Ohio

[73] Assignee: Snyder Laboratories, Inc., Dover, Ohio

[21] Appl. No.: 614,892

[22] Filed: May 29, 1984

[51] Int. Cl.$^4$ ............................................. A61M 1/00
[52] U.S. Cl. .................................... 604/321; 137/205
[58] Field of Search ............................... 604/317–321; 137/205; 141/48, 67

[56] References Cited

U.S. PATENT DOCUMENTS

| | | | |
|---|---|---|---|
| 3,774,611 | 11/1973 | Tussey et al. | 128/278 |
| 3,782,497 | 1/1974 | Bidwell et al. | 181/33 |
| 3,861,390 | 1/1975 | Schachet | 604/321 |
| 4,258,824 | 3/1981 | Kurtz et al. | 181/233 |
| 4,289,158 | 9/1981 | Nehring | 137/205 |
| 4,372,336 | 2/1983 | Cornell et al. | 604/319 |
| 4,406,657 | 9/1983 | Curutcharry | 604/328 |
| 4,439,189 | 3/1984 | Sargeant et al. | 604/317 |
| 4,439,190 | 3/1984 | Protzmann et al. | 604/319 |
| 4,455,141 | 6/1984 | Todd | 604/319 |
| 4,465,483 | 8/1984 | Weilbacher | 604/317 |
| 4,469,484 | 9/1984 | Kurtz et al. | 604/321 |

OTHER PUBLICATIONS

Medical Device & Diagnostic Industry (MD&DI) Mar. 1984–vol. 6–No. 3, Advertisement illustrating American Bentley's THORASEAL II Pleural Drainage System.

Primary Examiner—John F. Niebling
Assistant Examiner—Terryence Chapman
Attorney, Agent, or Firm—Margaret L. Geringer

[57] ABSTRACT

A chest drainage device is provided for draining fluid from a chest cavity. The drainage device has three chambers; a collection chamber, a liquid seal chamber, and a pressure regulating manometer chamber. The pressure regulating chamber includes a first column which has its upper end adapted to be open to communicate with the atmosphere, and a second column, which has a substantially larger cross-sectional area than the first column. A passage connects the bottom ends of the first and second columns to each other, so that the pressure regulating chamber is substantially U-shaped. In operation, air bubbles up through a body of liquid in the larger second column which produces a disturbing sound. The present invention provides a means for muffling this sound. The muffling means includes an elongated tube inside of and extending along the length of the first column of the pressure regulating chamber. This muffler tube serves to baffle the sound created by the bubbles which rise in the second, larger column of the pressure regulating chamber.

6 Claims, 10 Drawing Figures

FIG. 1

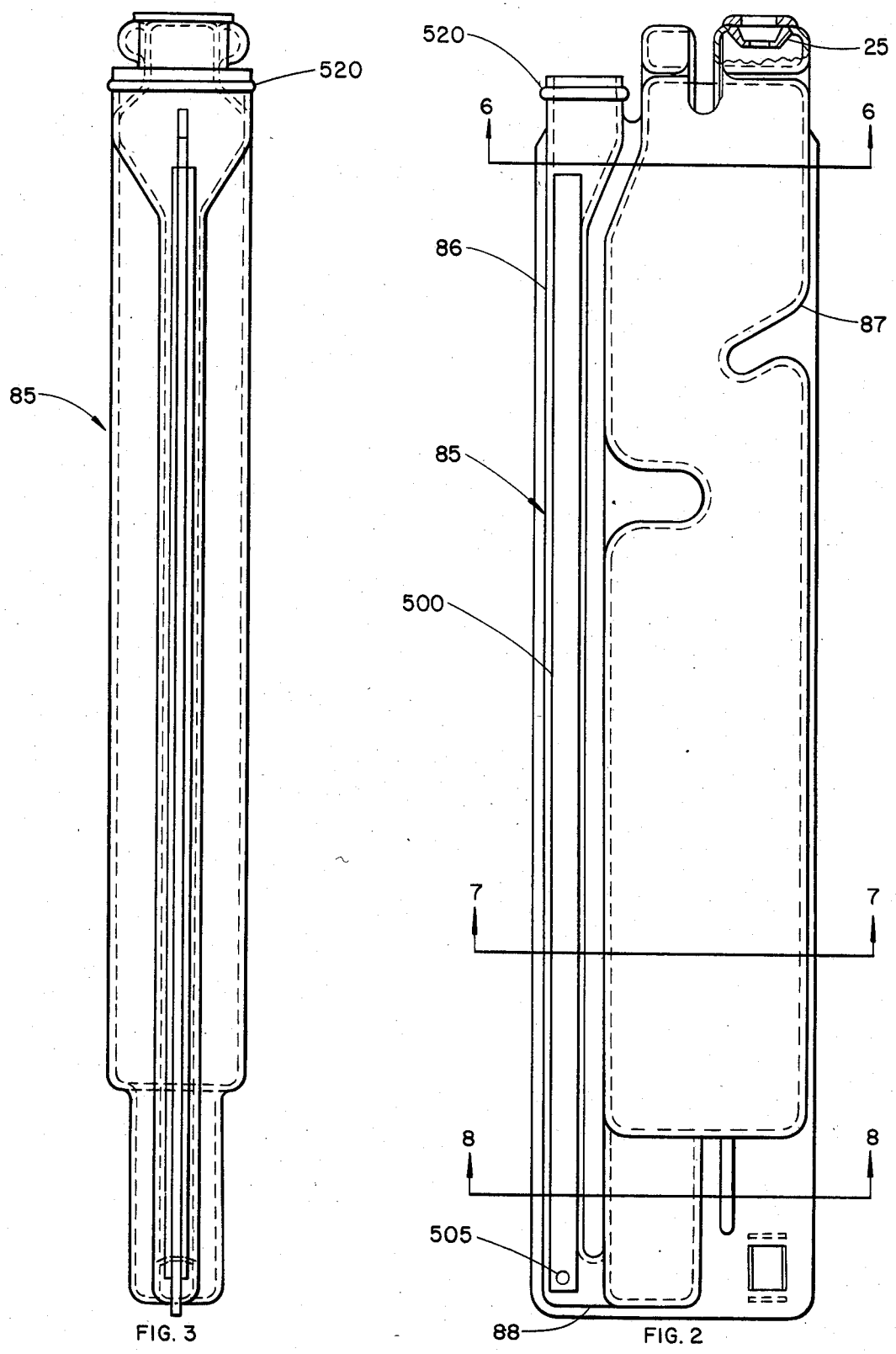

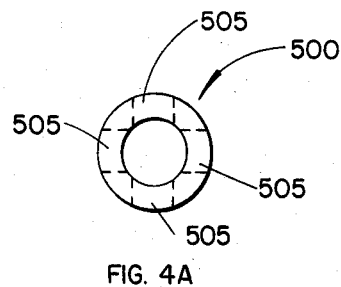
FIG. 4A
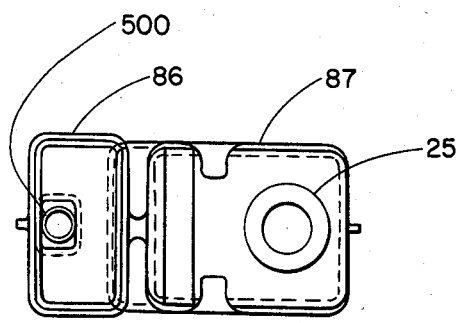
FIG. 5
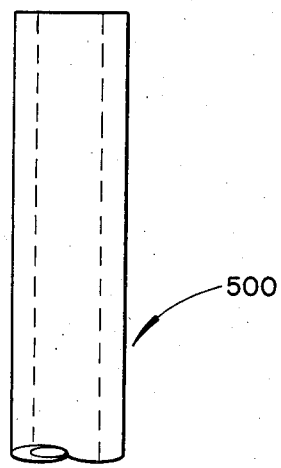
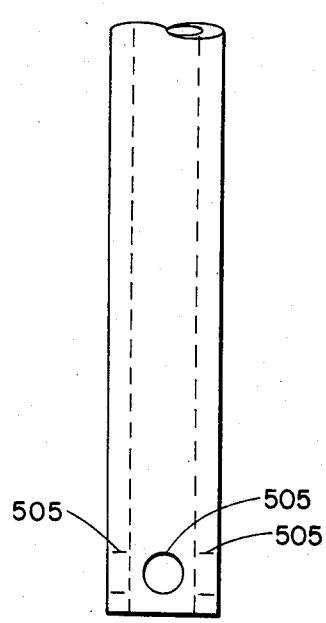
FIG. 4
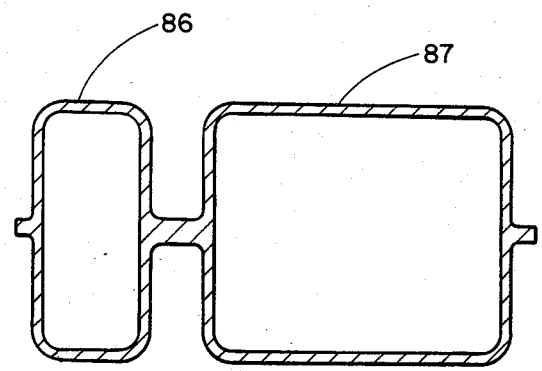
FIG. 6

CHEST DRAINAGE DEVICE WITH SOUND MUFFLING TUBE

BACKGROUND OF THE INVENTION

The present invention relates to chest drainage devices, and more particularly to such devices which include noise attenuating means. More particularly, the invention relates to such chest drainage devices used with vacuum, the devices comprising three sets of chambers: collection chamber, liquid seal chamber, and suction control (manometer or pressure regulation) chamber.

During operation of these devices, a gas bubbles through a body of liquid maintained in one of the chambers. For example, atmospheric air bubbles through a body of liquid provided in the suction control chamber to regulate the amount of vacuum applied to the collection chamber. The devices are useful in maintaining clear passages and cavities under operative and post operative conditions. Under such circumstances, the noise associated with the bubbling gas is frequently annoying.

Chest drainage devices generally of the type disclosed herein are known in the art. Applicant is aware of the following documents generally pertinent to chest drainage devices including muffling means:

U.S. Pat. No. 3,782,497 to Bidwell et al discloses a sound muffling device for an underwater (chest) drainage unit which includes a plug-like member which is inserted in the opening to the atmosphere from the manometer chamber. This member is provided with a tortuous passageway therethrough in order to muffle the sound emanating from the device by reason of the bubbling of gas through the water in the manometer (suction) chamber.

U.S. Pat. No. 4,258,824 to Kurtz et al discloses an apertured baffle plate in the large arm of the manometer chamber of an underwater drainage device. The baffle plate is provided with a plurality of fine holes therein, and serves to break up the air bubbles into small bubbles in order to effectively muffle the sounds emanating from the device during use.

U.S. Pat. No. 4,289,158 to Nehring discloses a chest drainage collection system which includes a means for attenuating noise in the suction control container. Column 11, line 61 through column 12, line 26 of the Nehring specification discusses this aspect of the invention. This system enables the user to choose whether or not to use the option of controlling suction quietly. Lines 11-15 of column 12 indicate that if quiet operation is desired, tube 126 (as referenced in FIGS. 16 and 17) is stoppered by a suitable cap or plug.

U.S. Pat. No. 4,439,189 to Sargeant et al discloses a chest drainage device which includes a vacuum control (suction) container. This chamber includes an inlet straw 92 extending from the upper portion of the container down to near the bottom. Water is placed in the vacuum control means to provide a specific head. When vacuum in the chest drainage device is sufficient to overcome the head pressure, air is sucked in through straw 92 to relieve the excess vacuum. A cap having slots is fixed to the end of the straw to break up the incoming air bubbles. The sound of these bubbles is psychologically bothersome to the patient and the cap helps to quiet the device. At the upper end of the straw, an adaptor tube is positioned to receive the straw. The adaptor tube is fixed into the bottom of a smaller container compartment. The container provides an easy pour access for filling the vacuum control through the straw. To prevent plugging of the vacuum control and to help eliminate the sound of air bubbles in the system, a loose-fitting cap 104 is positioned over the container. The cap is removed for the purpose of filling the vacuum control.

U.S. Pat. No. 4,439,190 to Protzmann et al discloses a chest drainage device in which the suction control (manometer) chamber 6 is, of course, normally subjected to a negative pressure, since it is connected to a source of vacumm. This manometer chamber includes a tube 70 which extends from the fill port 96 to the bottom of the manometer chamber. Because of the vacuum applied by the vacuum source, there can be a substantial amount of bubbling from this tube which can be disturbing and noisy. In accordance with the invention of Protzmann et al, means is provided for reducing the amount of bubbling in the suction chamber. This means includes a foot member 72 which is attached to the tube 70 in any convenient manner. The foot member is enlarged and at its terminal or toe end includes a plurality of relatively small openings 74 (FIG. 26). The foot is attached to the tube so that the air bubbles emanating from the foot through the openings hit the front wall of the device, and the bubbles will follow a circular path to minimize splashing within the chamber. This circular pattern also helps prevent fluid from entering the suction line.

OBJECTS OF THE INVENTION

It is a principle object of this invention to provide a chest drainage unit which provides a convenient and simple means for reducing to an acceptable level, the sound emanating from the chest drainage device by reason of the bubbling of gas through the water in the suction control (pressure regulating) chamber.

It is a further object of the invention to provide an improved chest drainage device.

SUMMARY OF THE INVENTION

The present invention provides a means for muffling the sound in a chest drainage device. The chest drainage unit is of the type including a collection chamber, a liquid seal chamber, and a pressure regulating chamber. The muffling means of the present invention is incorporated in the pressure regulating chamber and is suitable for a pressure regulating chamber which includes a first column which has its upper end adpated to be open to communicate with the atmosphere, and a second column, which has a substantially larger cross-sectional area than the first column. A passage connects the bottom ends of the first and second columns to each other, so that the pressure regulating chamber is substantially U-shaped.

The muffling means of the present invention includes an elongated tube inside of and extending along the length of the first column of the pressure regulating chamber. This muffler tube serves to baffle the sound created by the bubbles which rise in the second, larger column of the pressure regulating chamber. This muffler tube creates a plurality of smaller air passages in the first column in lieu of one larger passage. The sound of the bubbling is emitted through the walls of the pressure regulating chamber and up the first column. The sound coming out the first column is reduced by the insertion of the muffler tube. The muffling means of the present invention does not strive to break up the bubbles as does the above-mentioned device of Kurtz in U.S. Pat. No. 4,258,824. Instead, the present invention causes the sound waves to be weakened by out of phase vibrations of the air inside and outside the muffler tube which tends to cancel out the sound waves. Much of the sound tends to be transmitted through the smaller first column of the pressure regulating chamber since this first chamber is open to the atmosphere, whereas in operation, suction is applied by a vacuum pump through an opening at the top of the second column, creating a low pressure above the liquid in the second column. Sound does not travel well through the low pressure area, therefore, much of the sound of the bubbling tends to be transmitted through the smaller, first column. A cap means may be positioned over the upper end of the smaller first column of the pressure regulating chamber to further help eliminate the sound of air bubbles in the system.

The muffler tube has an additional advantage. It also may be used to remove excess water if the pressure regulating chamber is over filled. The cap is, of course, removed, and a catheter tipped syringe can be attached to the top of the muffler tube and liquid drawn out when suction is not being applied.

BRIEF DESCRIPTION OF THE DRAWINGS

These features and objects of the invention, as well as others, will become apparent to those skilled in the art by referring to the accompanying drawings in which:

FIG. 2 is a front elevational view of the pressure regulating chamber of the chest drainage device of FIG. 1;

FIG. 3 is an end elevational view of the pressure regulating chamber of FIG. 2;

FIG. 4 is an enlarged fragmentary, front elevational view of the muffler tube of the chest drainage device of FIG. 1;

FIG. 4A is a top view of the muffler tube of FIG. 4;

FIG. 5 is a top view of the pressure regulating chamber of FIG. 2;

FIG. 6 is a sectional view of the pressure regulating chamber of FIG. 2 taken along line 6—6 of FIG. 2;

DETAILED DESCRIPTION OF THE INVENTION

Figure 1:
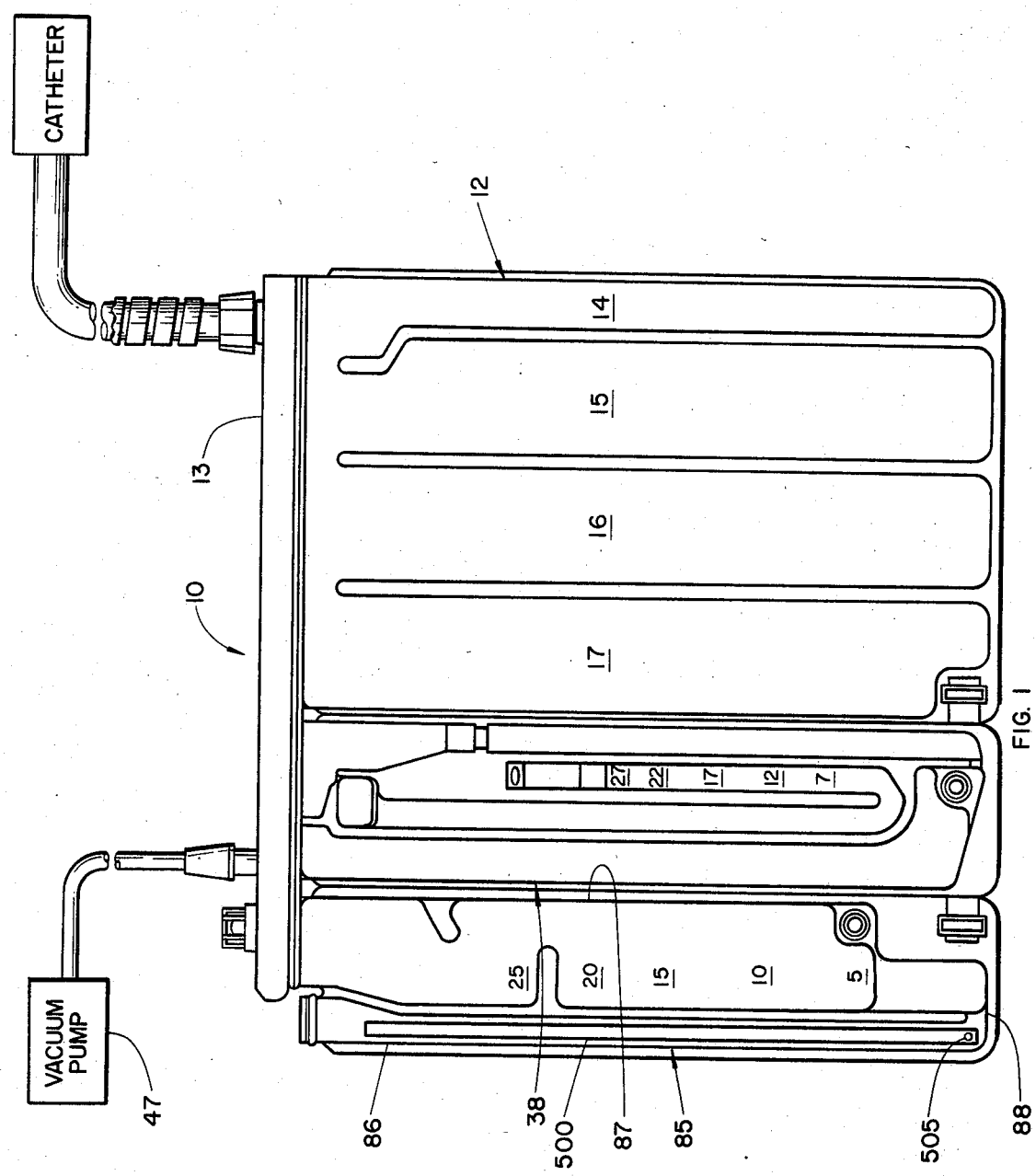
FIG. 1 is a front elevational view illustrating the muffling means of the present invention incorporated into a particularly advantageous embodiment of a chest drainage device.
Figure 7:
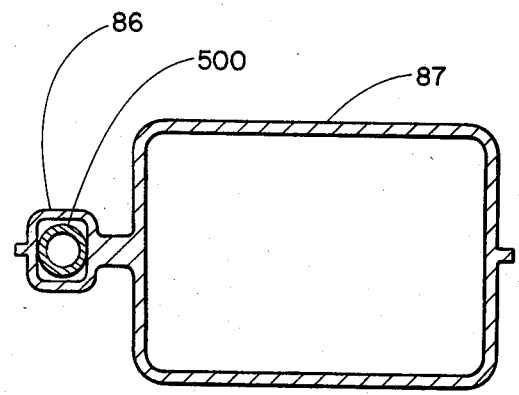
FIG. 7 is a sectional view of the pressure regulating chamber of FIG. 2 taken along line 7—7 of FIG. 2.
Figure 8:
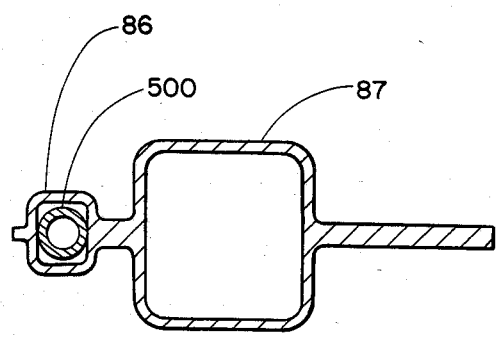
FIG. 8 is a sectional view of the pressure regulating chamber of FIG. 2 taken along line 8—8 of FIG. 2.

FIGS. 1-9 illustrate a chest drainage apparatus 10 for draining fluid from the pleural cavity of a patient, which incorporates a muffling means in accordance with the present invention. The chest drainage unit 10 of the present invention is of the type including a collection chamber 12, a liquid seal chamber 38 and a pressure regulating chamber 85. The collection chamber 12 is adapted to be connected in fluid communication with the pleural cavity of a patient. The liquid seal chamber 38 is in fluid communication with the collection chamber 12, and the pressure regulation chamber 85 is in fluid communication with the seal chamber 38, and is adapted to be connected to a source of suction 47. The muffling means of the present invention is incorporated in the pressure regulating chamber 85 and is suitable for the type of pressure regulating chamber which includes a first column 86 which has its upper end adapted to be open to communicate with the atmosphere, and a second column 87, which has a substantially larger cross-sectional area than the first column 86. A passage 88 connects the bottom ends of the columns 86 and 87 to each other, so that the pressure regulating chamber 85 is substantially U-shaped.

The present invention will be shown and described in conjunction with a particularly advantageous embodiment of a chest drainage unit such as that disclosed in U.S. Pat. No. 4,465,483 of Eugene E. Weilbacher, assigned to Snyder Laboratories, Inc. for "Modular Apparatus," which is incorporated herein by reference. It is noted that similar reference numbers have been used in the present application as in the above-noted application of Weilbacher to aid in coordinating the features of the present invention to the chest drainage device of Weilbacher. The invention of Weilbacher illustrates a chest drainage apparatus 10 having a modular configuration in which the various modular units and chambers are supported by a header 13. However, it is noted that the present invention is not limited to use with the embodiment of Weilbacher, as it is understood that the principles and objects of the present invention may be applicable to any suitable chest drainage device which includes a collection chamber, a liquid seal chamber and a substantially U-shaped pressure regulating manometer (suction control) chamber.

The muffling means of the present invention includes an elongated tube 500 inside of and extending substantially along the length of the first column 86 of the pressure regulating chamber 85. As shown in FIGS. 1, 2 and 4, muffler tube 500 includes one or more holes 505 at the distal end of the tube 500. The tube 500, as shown in FIGS. 4 and 4A, includes four holes 505 evenly spaced about the distal tip of tube 500. The holes 500 allow fluid communication from outside of the tube 500, so that the tube 500 doesn't seal off, such as if the distal end of tube 500 was in contact with the bottom, inner surface of column 86.

The muffler tube 500 serves to baffle the sound created by the bubbles which rise in the second column 87 of the pressure regulating chamber 85 during operation of the chest drainage unit 10. The muffler tube 500 creates a plurality of smaller air passages in the first column 86 in lieu of one larger passage, as shown more clearly in FIGS. 7 and 8. The cross-section of first column 86, as shown, is substantially rectangular. Therefore, if the tube 500 is cylindrical and its O.D. is approximately the same as the shorter inside length of the rectangular cross-section of column 86, as shown, tube 500 creates three smaller air passages in first column 86, with the tube I.D. being one passage, and the other two being created by the inner rectangular shape of first column 86 and by the O.D. of the tube 500. If the inner cross-sectional shape of first column 86 is square (not shown), and the inner length of the square cross-section is approximately the same as the O.D. of tube 500, then five smaller passages would be created.

In operation of the chest drainage device, suction is provided from a vacuum source 47 and is applied through a connection means which fits inside the opening in the gasket seal 25 on the top of second column 87.

This creates low pressure above the water in the larger, second column 87 of the pressure regulating chamber 85. Atmospheric air then pushes the water in the smaller, first column 86 down, forcing the water through passage 88 and into the larger, second column 87. The water level drops until air bubbles up through the water in the larger, second column 87. When the air bubbles reach the surface of the water, they break and the air continues up through the opening in gasket 25 and through the connection or communicating means 10 and to the suction (vacuum) source 47.

The sound of the bubbling is emitted through the walls of the pressure regulating chamber 85 and up the first column 86. The sound coming out of the first column is reduced by the insertion of the muffler tube 500. The sound waves are weakened by out of phase vibrations of the air inside and outside the muffler tube 500, which tends to cancel out the sound waves.

Figure 9:
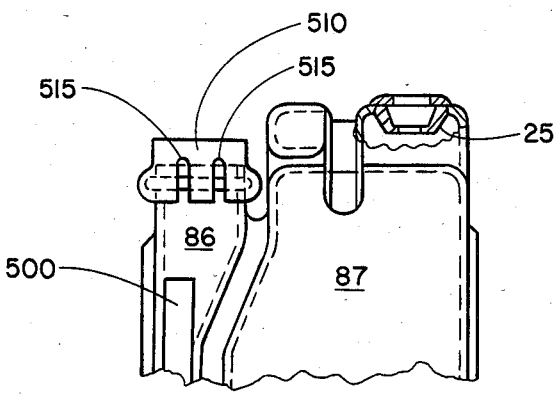
FIG. 9 is a fragmentary front elevational view of the pressure regulating chamber of FIG. 2 including a cap member covering the first column's opening to the atmosphere.

A cap 510, as shown in FIG. 9, may be positioned over the upper end of first column 86 which is open to the atmosphere. This cap 510 further helps to eliminate the sound of air bubbles in the system. The cap does not create an airtight seal, but in fact includes slots 515 around its peripheral rim. The cap conveniently snap fits about the beaded rim 520 of column 86. When the cap is positioned in place, slots 515 extend up past the upper most edge of column 86, providing some communication between the atmosphere and the inside of column 86.

When the cap 510 is not in place, the pressure regulation chamber 85 can be conveniently filled with the appropriate amount of water through the opening to atmosphere at the top of column 86. It is noted that the elongated muffler tube 500 has an additional advantage, in that it may also be used to remove excess water if the pressure regulating chamber 85 is over filled. With the cap 510 removed, a catheter tipped syringe (not shown) can be attached to the top of the muffler tube 500 and liquid drawn out when suction is not being applied. The proximal end of the tube 500 extends close enough to the atmospheric opening of column 86 to enable the syringe to reach the tube 500.

In assembling the chest drainage device 10, the muffler tube 500 is conveniently inserted into the first column 86 through the opening to the atmosphere at the top of column 86. The tube 500 may conveniently be bonded into the first column 86 by applying any suitable bonding agent to the outer surface of the tube on a portion of its O.D. that will be in contact with an inner wall surface of the first column 86. This bonding agent will securely locate the tube 500 in column 86, so that it does not get dislodged or fall out.

The muffler tube 500 may conveniently be made from a flexible polyvinyl chloride, while the various chambers of the chest drainage unit 10 may conveniently be made of butadiene styrene. However, it is understood that any suitable materials may be utilized.

While this invention has been described and exemplified in terms of a particularly advantageous embodiment, those skilled in the art can appreciate that modifications can be made without departing from the spirit and scope of this invention.

I claim:

1. A chest drainage device for removing fluids from the pleural cavity of a patient comprising:
   (a) a collection chamber adapted to be connected in fluid communication with the pleural cavity of a patient;
   (b) a liquid seal chamber in fluid communication with said collection chamber; and
   (c) a pressure regulation chamber in fluid communication with said seal chamber, and adapted to be connected to a source of suction; wherein said pressure regulation chamber includes a first column having an upper end including an opening to communicate with the atmosphere and a bottom end, and a second column larger than said first column having an upper end and a bottom end, and a passage connecting the bottom ends of said first and second columns, said first column being bounded by a plurality of side walls, and wherein said first column further includes an elongated muffler tube inside of and extending substantially along the length of said first column, said muffler tube contacting at least one of said side walls of the first column along the length of the tube, thus creating a plurality of elongated passageways within the first column, and wherein said muffler tube has a first end and a second end, said second end being located adjacent the bottom end of the first column.

2. The chest drainage device of claim 1 wherein said muffler tube includes one or more holes at the second end thereof.

3. The chest drainage device of claim 1 wherein the first end of said muffler tube extends at least close enough to said atmospheric opening of said first column, but without extending beyond the opening, to enable a catheter tipped syringe to be attached to the first end of said muffler tube to enable fluids to be withdrawn from said pressure regulation chamber.

4. The chest drainage device of claim 1 wherein said device further includes a removable cap for positioning over the opening in the upper end of said first column, said cap including a fluid communication means between the atmosphere and the internal chamber of said first column.

5. The chest drainage device of claim 4 wherein said fluid communication means includes one or more slots about the peripheral rim of said cap.

6. The chest drainage device of claim 1 wherein said muffler tube is in contact with at least two of said side walls of the first column along the length of the tube.

* * * * *